United States Patent
Silver

(10) Patent No.: US 12,329,843 B2
(45) Date of Patent: *Jun. 17, 2025

(54) DETERGENT COMPOSITIONS FOR WASHING URUSHIOL AND METHODS OF TREATING URUSHIOL INDUCED CONTACT DERMATITIS

(71) Applicant: THE WILLIAM M. YARBROUGH FOUNDATION, Peoria, IL (US)

(72) Inventor: Michael Edward Silver, Lake City, MI (US)

(73) Assignee: The William Yarbrough Foundation, Peoria, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/538,617

(22) Filed: Dec. 13, 2023

(65) Prior Publication Data

US 2024/0108568 A1 Apr. 4, 2024

Related U.S. Application Data

(63) Continuation of application No. 17/509,828, filed on Oct. 25, 2021, now Pat. No. 11,857,666, which is a
(Continued)

(51) Int. Cl.
*A61K 8/81* (2006.01)
*A61K 8/34* (2006.01)
(Continued)

(52) U.S. Cl.
CPC ............ *A61K 8/8147* (2013.01); *A61K 8/342* (2013.01); *A61K 8/345* (2013.01); *A61K 8/42* (2013.01);
(Continued)

(58) Field of Classification Search
CPC .......... A61P 29/00; A61P 17/00; A61P 17/04; A61P 37/00; A61P 37/02; A61P 37/04; A61P 1/16; A61P 17/06; A61P 35/00; A61P 17/02; A61P 17/16; A61P 37/08; A61P 39/00; A61P 17/08; A61P 17/10; A61P 31/10; A61P 17/14; A61P 25/20; A61P 27/02; A61P 43/00; A61P 9/10; A61K 2300/00; A61K 9/0014; A61K 31/05; A61K 31/195; A61K 31/20; A61K 31/185; A61K 9/06; A61K 36/81; A61K 45/06; A61K 31/403; A61K 31/4035; A61K 47/08; A61K 47/10; A61K 47/22; A61K 8/39; A61K 9/0053; A61K 2236/30; A61K 2236/53; A61K 31/045; A61K 31/125; A61K 31/765; A61K 36/899; A61K 47/26; A61K 9/1075; A61K 2800/28; A61K 2800/31; A61K 2800/75; A61K 31/015; A61K 31/19; A61K 31/315; A61K 31/40; A61K 31/4164; A61K 31/451; A61K 31/454; A61K 31/485; A61K 31/496; A61K 31/537; A61K 31/5377; A61K 31/5575; A61K 31/575; A61K 31/675; A61K 31/69; A61K 33/14; A61K 36/28; A61K 36/67; A61K 47/06; A61K 47/18; A61K 47/24; A61K 47/32; A61K 47/40; A61K 47/44; A61K 8/25; A61K 8/43; A61K 8/44; A61K 8/45; A61K 8/49; A61K 8/4946; A61K 8/602; A61K 8/86; A61K 9/0043; A61K 9/08; A61K 9/107; A61K 9/113; A61K 9/12; A61K 9/20; A61K 9/2009; A61K 9/2013; A61K 9/2018; A61K 9/2054; A61K 9/4808; A61K 9/4858; A61K 2800/244; A61K 31/085; A61K 31/197; A61K 31/381;
(Continued)

(56) References Cited

U.S. PATENT DOCUMENTS 6,423,746 B1  7/2002  Yarbrough et al.
7,008,963 B2  3/2006  Yarbrough
(Continued)

FOREIGN PATENT DOCUMENTS

| ES | 2688360 T3 | 11/2018 |
| WO | 0202104 A1 | 1/2002 |
| WO | 2015171986 A1 | 11/2015 |

OTHER PUBLICATIONS

United States Patent and Trademark Office, Non-Final Office Action issued in connection with U.S. Appl. No. 16/825,790, dated Nov. 4, 2020, 12 pages.
United States Patent and Trademark Office, Non-Final Office Action issued in connection with U.S. Appl. No. 16/795,247, dated May 11, 2020, 13 pages.
(Continued)

*Primary Examiner* — Audrea B Coniglio
*Assistant Examiner* — Audrea Buckley
(74) *Attorney, Agent, or Firm* — Nyemaster Goode P.C.

(57) ABSTRACT

A composition and a method of washing urushiol off a surface. The composition includes a first solely $C_{12}$ surfactant and a second solely $C_{12}$ surfactant that are each in a non-buffered composition and the composition is free of each of the following: (1) any nonylphenol ethoxylate, (2) any pharmaceutically active drug or prodrug, or (3) any salt that affects the functional characteristics of either of the first solely C12 surfactant or the second solely C12 surfactant, (4) any salt in granular form, and (5) any ethoxylate added as a separate component and not part of the non-ionic polyethylene glycol ether of a mixture of synthetic C12-C15 fatty alcohols with an average of 9 moles of ethylene oxide.

20 Claims, No Drawings

Related U.S. Application Data continuation of application No. 16/795,247, filed on Feb. 19, 2020, now Pat. No. 11,154,486.

(60) Provisional application No. 62/976,894, filed on Feb. 14, 2020.

(51) Int. Cl.
| | |
|---|---|
| *A61K 8/42* | (2006.01) |
| *A61K 8/44* | (2006.01) |
| *A61K 8/60* | (2006.01) |
| *A61K 8/86* | (2006.01) |
| *A61K 8/894* | (2006.01) |
| *A61Q 19/10* | (2006.01) |

(52) U.S. Cl.
CPC ............ *A61K 8/44* (2013.01); *A61K 8/60* (2013.01); *A61K 8/86* (2013.01); *A61K 8/894* (2013.01); *A61Q 19/10* (2013.01); *A61K 2800/30* (2013.01); *A61K 2800/41* (2013.01); *A61K 2800/596* (2013.01)

(58) Field of Classification Search
CPC .. A61K 31/415; A61K 31/425; A61K 31/515; A61K 47/14; A61K 8/4953; A61K 8/4973; A61K 9/4883
See application file for complete search history.

(56) References Cited

U.S. PATENT DOCUMENTS

| | | | |
|---|---|---|---|
| 7,858,570 B2 | 12/2010 | Hare | |
| 8,067,358 B1 | 11/2011 | Smith et al. | |
| 11,154,486 B2 * | 10/2021 | Silver | ............ A61K 8/342 |
| 11,191,708 B2 * | 12/2021 | Silver | ............ A61K 8/8147 |
| 2002/0183284 A1 | 12/2002 | Yarbrough | |
| 2006/0147405 A1 | 7/2006 | Yarbrough | |
| 2006/0147484 A1 | 7/2006 | Hestand | |
| 2006/0177400 A1 | 8/2006 | Yarbrough | |
| 2006/0177406 A1 | 8/2006 | Niazi et al. | |
| 2006/0275333 A1 | 12/2006 | Trimble et al. | |
| 2007/0059268 A1 | 3/2007 | Magee | |
| 2008/0107742 A1 | 5/2008 | Hare | |
| 2008/0194662 A1 | 8/2008 | Kunin | |
| 2009/0191248 A1 | 7/2009 | Hoffman et al. | |
| 2014/0377337 A1 | 12/2014 | Steigerwalt, Jr. | |
| 2015/0057255 A1 | 2/2015 | Zhang et al. | |
| 2016/0338973 A1 | 11/2016 | Sonti et al. | |
| 2016/0376263 A1 | 12/2016 | Patron et al. | |
| 2017/0087199 A1 | 3/2017 | Patron et al. | |
| 2019/0216779 A1 | 7/2019 | Basta et al. | |

OTHER PUBLICATIONS

Pankaj Karande et al., Synergistic effects of chemical enhancers on skin permeability: A case of sodium auroylsarcosinate and sorbitan monolaurate, European Journal of Pharmaceutical Scienes 31 (2007), pp. 1-7.

Rhein et al., "Interfacial Phenomena in Biological Systems", Surfactant Science Series, 1991, pp. 46-48, vol. 39.

* cited by examiner

DETERGENT COMPOSITIONS FOR WASHING URUSHIOL AND METHODS OF TREATING URUSHIOL INDUCED CONTACT DERMATITIS

CROSS-REFERENCE TO RELATED APPLICATIONS

This application is a continuation of U.S. patent application Ser. No. 17/509,828, filed on Oct. 25, 2021, entitled "DETERGENT COMPOSITIONS FOR WASHING URUSHIOL AND METHODS OF TREATING URUSHIOL INDUCED CONTACT DERMATITIS." U.S. patent application Ser. No. 17/509,828 is a continuation of U.S. application Ser. No. 16/795,247, now U.S. Pat. No. 11,154,486, filed on Feb. 19, 2020, entitled "Detergent Compositions for Washing Urushiol and Methods of Treating Urushiol Induced Contact Dermatitis." U.S. patent application Ser. No. 16/795,247 claims priority to and the benefit of U.S. Provisional Application Ser. No. 62/976,894, filed on Feb. 14, 2020, entitled "Detergent Compositions for Washing Urushiol and Methods of Treating Urushiol Induced Contact Dermatitis." The disclosures of all of the above patent applications and patents are hereby incorporated herein by reference in their entirety.

BACKGROUND

Urushiol is an oily mixture of organic compounds. It is a yellow liquid. It is soluble in ethanol, diethyl ether, and benzene. Urushiol is a mixture of several closely related organic compounds. Each consists of a catechol substituted in the 3 positions with a hydrocarbon chain that has 15 or 17 carbon atoms. The hydrocarbon group may be saturated or unsaturated. The exact composition of the mixture varies, depending on the plant source. Whereas western poison oak urushiol contains chiefly catechols with C17 side-chains, poison ivy and poison sumac contain mostly catechols with C15 sidechains. Typically, Urushiol has the chemical structure below

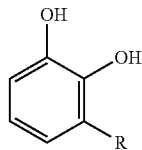

where R is one of the following: $(CH_2)_{14}CH_3$ or $(CH_2)_7CH=CH(CH_2)_5CH_3$; $(CH_2)_7CH=CHCH_2CH=CH(CH_2)_2CH_3$; $(CH_2)_7CH=CHCH_2CH=CHCH=CHCH_3$; or $(CH_2)_7CH=CHCH_2CH=CHCH_2CH=CH_2$.

Urushiol-induced contact dermatitis (also called *Toxicodendron* dermatitis and Rhus dermatitis) is produced by the oil urushiol. Urushiol is contained in various plants, including the plants of the family Anacardiaceae, especially the species *Toxicodendron*, which includes poison ivy, poison oak, and poison sumac. Other plants in the family Anacardiaceae, include mango, Rengas tree, Burmese lacquer tree, India marking nut tree, and the shell of the cashew nut. A few unrelated plants, such as *Ginkgo biloba*, also contain urushiol. Poison ivy, poison oak, and poison sumac grow in wooded or marshy areas throughout North America. The plants aren't really poisonous. The urushiol causes an itchy, blistering rash after it touches a human's skin. Even slight contact, like brushing up against the leaves, can leave the oil behind. Poison sumac is a shrub or tree. Poison ivy and poison oak grow as vines or shrubs.

Symptoms of urushiol-induced contact dermatitis include itching, inflammation, oozing, and in severe cases, a burning sensation. Urushiol-induced contact dermatitis is contracted by contact with a plant or any other object containing urushiol oil. The oil adheres to almost anything with which it comes in contact, such as skin; essentially any fabric product such as towels, blankets, and clothing; and gear such as backpacks. Any surface contacting the plant and then contact with the skin typically causes exposure to the oil. Normally, it takes about 24 hours for the rash to first appear. Oftentimes, the rash will worsen over a period of a few days. When someone has a severe reaction to urushiol a prednisone prescription is necessary to stop skin damage, especially if the eyes or other sensitive part of the human anatomy has been exposed to the oil or exhibits an allergic reaction to the oil. The urushiol induced dermatitis rash often persists typically for one to two weeks but in some cases can last as long as five weeks. Since the skin reaction is an allergic one, some people may mount progressively stronger reactions after repeated exposures. People vary greatly in their sensitivity to urushiol. In up to 30% of people, urushiol does not trigger an immune response; however, if it does, the rash and effects are irritating and can be very serious. There are various drug and active pharmaceuticals that have been developed or proposed for use in connection with the treatment of these symptoms/effects. Typically, treatment for urushiol induced contact dermatitis includes first stopping contact with the urushiol source or oil containing surface and later reducing the pain and/or itching. The primary treatment employed is typically washing of the skin with soap, cool water and friction as soon as possible after the discovery that the skin has been exposed to urushiol.

There are various previously used treatments of urushiol-induced contact dermatitis including washing compositions or compositions that medicinally temporarily reduce the itching and perhaps some of the other symptoms caused by contact with urushiol. Most such compositions use ethoxylate is a nonylphenol ethoxylate such as nonoxynol 9. Nonoxynol 9 is a surfactant spermicide used for contraception in spermicidal creams, jellies, foams, gel, and lubricants. It is also used in conjunction with other methods of contraception, including condoms, cervical caps and diaphragms. It is also used in certain detergents and other products. However, there are significant environmental problems associated with the use of nonylphenol ethoxylate in any composition that will be washed into an aquatic environment or into a septic or water treatment system. In particular, the Environmental Protection Agency (EPA) in the U.S. has noted that nonylphenol (NP) is persistent in the aquatic environment, moderately bioaccumulative, and extremely toxic to aquatic organisms. Furthermore, NP has also been shown to exhibit estrogenic properties in in vitro and in vivo assays. NP's main use is in the manufacture of nonylphenol ethoxylates (NPEs). Under the Toxic Substances Control Act (TSCA), in 2014, the EPA proposed a significant new use rule (SNUR) to require Agency review before a manufacturer begins or resumes use of 15 NPs and NPEs.

The use of NPEs in household laundry detergents is thought to have been completely phased out (U.S. EPA 2010b). Proctor and Gamble, the leading household liquid laundry detergent vendor in the U.S. (Statista 2017), stopped using them around 2005 (Proctor & Gamble 2005) and Walmart and Target added them to their priority list of chemicals for their suppliers to remove from products in 2015 and 2016, respectively. The use of laundry detergents containing NPEs by industrial laundries has also declined. In 2010, the Textile Retail Services Association (TRSA), representing approximately 98 percent of industrial laundry facilities in the United States, entered into a voluntary agreement with EPA to phase out the use of NPEs in detergents by 2014 (TRSA 2010). While significant progress has been made towards implementing this agreement, U.S. EPA estimates it only covers approximately 50 percent of NPE laundry detergent use, and the complete phase-out has not been confirmed. In fact, nonoxynol-9 carries with it a GHS Hazard Statement H411 that it is toxic to aquatic life with long lasting effects.

SUMMARY

An aspect of the present disclosure is generally directed to a method of washing urushiol off the surface of human skin that includes the steps of: applying a detergent composition to at least an area of a human's skin exposed to urushiol; washing the area; and rinsing the detergent composition from the area. The detergent composition is typically a non-buffered composition and is typically free of each of the following: (1) any nonylphenol ethoxylate, (2) any pharmaceutically active drug or prodrug, (3) any salt that affects the functional characteristics of either of the solely C12 surfactants, and (4) any salt in granular form.

Another aspect of the present disclosure is generally directed toward a method of washing urushiol from the surface of human skin comprising the steps of: applying a detergent composition to at least an area of a human's skin exposed to urushiol; washing the area; and rinsing the detergent composition from the area. The detergent composition may consist essentially of: water; a hydrophilic and cross-linked polyacrylic acid polymer; at least one type of bio-degradable bead having a maximum particle size of 300 microns; a silicone copolyol wetting agent; a first solely C12 surfactant is a non-ionic solely C12 surfactant; a second solely C12 surfactant is an anionic solely C12 surfactant; a non-ionic polyethylene glycol ether of a mixture of synthetic C12-15 fatty alcohols with an average of 9 moles of ethylene oxide; a quaternary ammonium salt; disodium EDTA; and sodium hydroxide. The detergent composition is typically a non-buffered composition and is typically free of each of the following: (1) any nonylphenol ethoxylate, (2) any pharmaceutically active drug or prodrug, (3) any salt that affects the functional characteristics of either of the solely C12 surfactants, and (4) any salt in granular form.

Yet another aspect of the present disclosure is a method of washing urushiol off the surface of human skin comprising the steps of: applying a composition to at least an area of a human's skin exposed to urushiol; washing the area; and rinsing the composition from the area and the rinsed composition does not affect marine life reproduction. The composition may consist of: water; a hydrophilic and cross-linked polyacrylic acid polymer; at least one type of bio-degradable bead having a maximum particle size of 300 microns; a silicone copolyol wetting agent; a first solely C12 surfactant is a non-ionic solely C12 surfactant; a second solely C12 surfactant is an anionic solely C12 surfactant; a non-ionic polyethylene glycol ether of a mixture of synthetic C12-15 fatty alcohols with an average of 9 moles of ethylene oxide; a quaternary ammonium salt; disodium EDTA; and sodium hydroxide. The composition is typically a non-buffered composition and is also typically free of each of the following: (1) any nonylphenol ethoxylate, (2) any pharmaceutically active drug or prodrug, (3) any salt that affects the functional characteristics of either of the solely C12 surfactants, and (4) any salt in granular form.

These and other aspects, objects, and features of the present invention will be understood and appreciated by those skilled in the art upon studying the following specification, claims, and appended drawings.

DETAILED DESCRIPTION

It is to be understood that the invention may assume various alternative orientations, except where expressly specified to the contrary. It is also to be understood that the specific devices and processes illustrated in the attached drawings, and described in the following specification are simply exemplary embodiments of the inventive concepts defined in the appended claims. Hence, specific dimensions and other physical characteristics relating to the embodiments disclosed herein are not to be considered as limiting, unless the claims expressly state otherwise. All ranges and parameters, including but not limited to percentages, parts, and ratios, disclosed herein are understood to encompass any and all sub-ranges assumed and subsumed therein, and every number between the endpoints. For example, a stated range of "1 to 10" should be considered to include any and all sub-ranges beginning with a minimum value of 1 or more and ending with a maximum value of 10 or less (e.g., 1 to 6.1, or 2.3 to 9.4), and to each integer (1, 2, 3, 4, 5, 6, 7, 8, 9, 10) contained within the range. In this specification and the appended claims, the singular forms "a," "an" and "the" include plural reference unless the context clearly dictates otherwise. All combinations of method or process steps as used herein can be performed in any order, unless otherwise specified or clearly implied to the contrary by the context in which the referenced combination is made.

The various embodiments of the urushiol treating compositions of the present disclosure may also be substantially free of any ingredient or feature described herein, provided that the remaining composition still contains all of the required ingredients or features as described herein. In this context, and unless otherwise specified, the term "substantially free" means that the selected composition contains less than a functional amount of the optional ingredient, typically less than 1%, including less than 0.5%, including less than 0.1%, and also including zero percent, by weight of such optional or selected essential ingredient.

The compositions of the present disclosure described herein, including but not limited to compositions for washing urushiol off of skin, compositions for treating urushiol induced contact dermatitis and methods of treating urushiol on the skin and removing it as well as methods of treating urushiol induced contact dermatitis, and corresponding manufacturing methods may comprise, consist of, or consist essentially of the elements of the products as described herein, as well as any additional or optional element described herein or otherwise useful in topical wash product applications. Typically, the compositions of the present disclosure are free of pharmaceutically active ingredients/drug(s) or prodrugs, sodium chloride (NaCl)/granulated salt, any salt in granular form that would essentially operate as an exfoliating or scrubbing agent when the detergent compositions of the present disclosure are on the surface of a person's skin or clothing, and/or nonylphenol ethoxylate(s) such as Nonxyl-9. The detergent compositions typically do not include the foregoing components, but the claims of this application do not exclude them unless specifically indicated.

"Consisting essentially of" in the context of the claims of this application limits the scope of a claim or claim element to the specified materials or steps "and those that do not materially affect the basic and novel characteristic(s)" of the claimed invention as would be known by those of ordinary skill in the art whether or not such a composition is disclosed in the application or not as affecting the basic and novel characteristic. For example, in the case of a salt (NaCl), this ingredient, if added to compositions of the present disclosure containing the synergistic combination of C12 surfactants discussed herein, materially affects the surface tension and other performance characteristics of the surfactants of the present disclosure.

To the extent that the term "includes" or "including" is used in the specification or the claims, it is intended to be inclusive in a manner similar to the term "comprising" as that term is interpreted when employed as a transitional word in a claim. Furthermore, to the extent that the term "or" is employed (e.g., A or B) it is intended to mean "A or B or both." When the Applicant intends to indicate "only A or B but not both" then the term "only A or B but not both" will be employed. Thus, use of the term "or" herein is the inclusive, and not the exclusive use. Also, to the extent that the terms "in" or "into" are used in the specification or the claims, it is intended to additionally mean "on" or "onto."

Typical Components of the Detergent/Cleaning Compositions of the Present Disclosure The overall detergent compositions of the present disclosure typically include water, more typically deionized water. Water can be included in an amount of from about 40-60 weight percent of the overall compositions. Water is a part of some of the raw material components of the detergent composition and added as a separate additive. The typical formulas for the detergent compositions of the present disclosure have water added independently in an amount of about 40-60 weight percent water as a separate and independent component. Water is also typically contributed by two other components of the compositions of the present disclosure. However, water is not necessarily required and can be utilized in lower amounts as well.

Surprisingly, it is presently believed that the efficacy of the presently disclosed detergent compositions is in large part due to the use of a plurality of solely twelve carbon chain length surfactants (C12 surfactants) that work together to remove urushiol more effectively than other individual surfactants and typically at least as effectively as, if not more effectively than, prior overall compositions that included nonylphenol ethoxylates and/or pharmaceutically active ingredients. While C12-15 Pareth-9, which contains a mixture of C12, C13, C14 and C15 components, is a surfactant that may be used in the detergent compositions of the present disclosure, it is not a solely C12 surfactant ingredient because it has a range of surfactants in it. Two particular solely C12 surfactants that have been found to surprisingly provide synergistic results when combined with one another, in particular when the detergent composition is without a nonylphenol ethoxylate, which previously was thought to be a necessary component of many such compositions, include: SPAN 20™ (sorbitan laurate)(sorbitan monolaurate) and sodium lauroyl sarcosinate. SPAN 20™ is a sorbitan ester and is a biodegradable surfactant based on a natural fatty acid (lauric acid) and sugar alcohol sorbitol. This sorbitan ester is highly effective at forming oil in water emulsions, particularly when used with its ethoxylated derivative, TWEEN® 20. Sorbitan monolaurate is a non-ionic surfactant that is a mixture of esters formed from the fatty acid lauric acid and polyols derived from sorbitol, including sorbitan and isosorbide and has a chemical structure of $C_{18}H_{34}O_6$. Sodium lauroyl sarcosinate (INCI), also known as sarkosyl, is an anionic surfactant derived from sarcosine. It is a sodium salt of lauroyl sarcosine. It generally conforms to the formula:

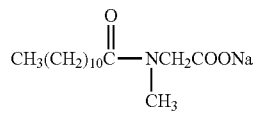

The percentage of sodium lauroyl sarcosinate is generally a maximum of 1.5% of the ingredient itself. It is typically a white solid in pure form and produces a colorless to light yellow aqueous solution. When used, the sorbitan monolaurate is typically present in an amount of from about 0.5 percent to as much as about 50 percent by weight of the overall composition, more typically in an amount of about 2.0% or 10% by weight of the overall composition. The sodium lauroyl sarcosinate is typically added in the form of an aqueous solution with 30% of the solution being sodium lauroyl sarcosinate. Sodium lauroyl sarcosinate is typically present in slightly lower amounts than the amount of the sorbitan monolaurate in the overall detergent compositions of the present disclosure, but can be used in higher amounts as well. The sodium lauroyl sarcosinate and sorbitan monolaurate are present in a ratio based on the percent of active ingredient in the overall detergent composition in a ratio range of from 1 part sodium lauroyl sarcosinate to up to 2.5 parts sorbitan monolaurate. While lower amount of sodium lauroyl sarcosinate than sorbitan monolaurate are typically used, amounts of sodium lauroyl sarcosinate may be used in higher amounts as well including up to 10%, 15%, 20% or even 50% by weight of the overall detergent composition. The amount of sodium lauroyl sarcosinate is typically from about 1.0% to about 10% by weight of the overall composition. When higher amounts are included, less water is typically added as a separate and independent component and possibly, but less preferentially, lower amounts of other ingredients/components employed.

The detergent compositions of the present disclosure may include a quaternary ammonium salt such as Quaternium-15. It acts as an antimicrobial agent/preservative because it acts as a formaldehyde releaser. Any known preservative may be used instead of or in addition to the quaternary ammonium salt. Another component that is typically present in the compositions of the present disclosure is C12-15 Pareth-9. C12-15 Pareth-9 is a polyethylene glycol ether of a mixture of synthetic C12-15 fatty alcohols with an average of 9 moles of ethylene oxide. It is a non-ionic surfactant. It is a surfactant that has a component of C12 surfactant, but is not solely composed of a C12 surfactant.

The detergent compositions of the present disclosure also typically contain a CARBOPOL®, which is a high molecular weight, hydrophilic and cross-linked polyacrylic acid polymer. This physical hydrogel presents a three-dimensional polymer network that is swollen by water, and presents temporary, reversible inter-chain entanglements that are stronger when compared to chemical hydrogels. The particularly preferred CARBOPOL® of the present disclosure is CARBOPOL® 980 polymer, which is a white powder, cross-linked polyacrylic acid that is polymerized in a toxicologically-preferred co-solvent system. It is an extremely efficient rheology modifier capable of providing high viscosity and forms sparkling clear gels or hydro-alcoholic gels and creams. CARBOPOL® 980 has a viscosity of 40,000-60,000 cP (0.5% at pH 7.5) and a monomer molecular weight of 72.02 g/mol.

The overall detergent composition is typically at a pH of from about 5.5 to 7.0, is typically un-fragranced, white to off-white and an opaque creamy lotion. When scrubbing beads are employed in the composition the scrubbing breads make the composition have a gritty texture.

When one or more kinds of scrubbing beads are employed in connection with the compositions of the present disclosure, the beads are typically beads that are bio-degradable beads. However, polyethylene beads may also be employed as well. Sasol Ltd. DECORNEL® 300 synthetic wax polymer beads or Micro Powders Inc. SYNSCRUB® 50PC high molecular weight synthetic wax polymer beads or Low Density Polyethylene (LDPE) beads may be used. The synthetic wax used in DECORNEL® and SYNSCRUB® products is biodegradable. As such, this material is preferred over polyethylene beads, which have a very long degradation timetable comparatively—especially since the compositions of the present disclosure are skin washing compositions where the material is washed into the water treatment system/plumbing systems. The use of biodegradable beads in some form allows the detergent compositions of the present disclosure to completely biodegrade in ambient environment after 2 years. Additionally, the at least one type of bio-degradable beads of the present disclosure typically biodegrades in an ambient environment by 33.8% after 86 days according to the Organization for Economic Co-operation and Development Test Guideline 302 C entitled Inherent Biodegradability: Modified MITI Test (II).

DECORNEL® 300 by Sasol acts as a consistency regulator, exfoliating and cleansing agent. It is a nonpolar, white, tasteless and odorless wax bead. It is a blend consisting predominantly of saturated n-alkanes, highly refined. It is available in 50-300 μm particle size. It is 100% hydrophobic and preservative-free. It is non-ionic and has no impact on the pH value of the overall composition when incorporated into compositions of the present disclosure. It offers consistent high quality and removes dead cells smoothly. It can outperform polyethylene beads in face, hand and foot scrubs as well as toothpaste. DECORNEL® 300 is synthesized from carbon monoxide and hydrogen in accordance with the Fischer-Tropsch method. It can replace plant waxes, hydrogenated fats and other hard base substances in products. As stated above, it does not influence the pH-value and can be applied in formulas with a pH-value of 3-11. It is a very pure product and inherently primarily biodegradable in the terms of the OECD Test 301-B/302-C. DECORNEL® 300 has a shelf life of 60 months.

SYNSCRUB® 50PC is a synthetic wax powder. It is designed for use as an economical exfoliating agent and has an irregular particle shape which produces the same high performance as commonly used irregular particle shape polyethylene powders. It is, however, biodegradable. SYNSCRUB® 50PC has a maximum mesh side of 50 and a maximum particle size of 297 microns. Its density at 77° F. is 0.95.

Another component of the typical detergent composition is a PEG-12 dimethicone, which belongs to the class of dimethyl-methyl(polyethyleneoxide) siloxanes. It is presently believed that any dimethyl-methyl(polyethyleneoxide) siloxane may be used or a plurality of dimethyl-methyl (polyethyleneoxide) siloxanes may be used in the detergent compositions of the present disclosure. When used, the PEG-12 dimethicone (or one or more dimethyl-methyl(polyethyleneoxide) siloxane) is typically present in an amount of from about 0.8% by weight to about 1.2% by weight of the overall detergent composition. PEG-12 dimethicone is a silicone glycol copolymer soluble in water, alcohol, and hydro-alcoholic systems. It acts as a surface tension depressant, wetting agent, emulsifier and foam builder. PEG-12 dimethicone gives a stable foam. The PEG-12 dimethicone is a silicone copolyol wetting agent. If a wetting agent is used, it must be soluble in water and not dispersible or insoluble, which could result in deposits that clog or block hair follicles into which urushiol has migrated. The wetting agent's hydrophilic-lipophilic balance is typically 10 or higher on the HLB scale from 0 to 20.

The detergent compositions of the present disclosure also typically include disodium EDTA. Disodium EDTA is also known as Disodium ethylenediaminetetraacetic acid. Disodium EDTA is used as a chelating agent that sequesters a variety of polyvalent cations such as calcium. Chelating agents are chemical compounds that react with metal ions to form a stable, water-soluble complex. Chelating agents have a ring-like center which forms at least two bonds with the metal ion allowing it be excreted. Disodium EDTA has a molecular weight of 138.22 g/mol and is a white crystalline powder. Disodium EDTA is typically included in the compositions of the present disclosure in an amount of from about 0.8% to 1.2% by weight of the overall composition.

Finally, while not necessary, the detergent compositions of the present disclosure typically also include an amount of sodium hydroxide (25%). The sodium hydroxide is typically present in an amount of the overall composition to neutralize CARBOMER® and achieve a desirable pH.

Possible Additional Ingredients

It will be understood by one having ordinary skill in the art that construction of the described invention and other components is not limited to any specific material. Other exemplary embodiments disclosed herein may be formed from a wide variety of materials, unless described otherwise herein. The urushiol compositions and methods of treatment of the present disclosure may further comprise additional components that may modify the physical, chemical, aesthetic or processing characteristics of the formulas or serve as pharmaceutical or additional components when used in a targeted population. Non-limiting examples of such optional ingredients include preservatives, anti-oxidants, emulsifying agents, colorants, and related derivatives, thickening agents and stabilizers, and other additive or synergistic ingredients that will be appreciated in the art of urushiol treating composition formulation. However, the compositions of the present disclosure, as discuss above, will typically not include and are typically free of any nonylphenol ethoxylate, more typically any ethoxylate that is not part of the nonionic polyethylene glycol ether of a mixture of synthetic C12-C15 fatty alcohols with an average of 9 moles of ethylene oxide; a granulated salt; or a pharmaceutically active component used to treat urushiol including, but not limited to neurokinin-1 (NK-1) antagonists, such as serlopiltant. Additionally, the detergent compositions of the present disclosure also typically an unbuffered detergent composition. The detergent compositions of the present disclosure also typically do not include any surfactant component that interferes with or alters the functional characteristics of the one or more solely C12 surfactants employed in the detergent compositions.

It is also to be understood that variations and modifications can be made on the aforementioned detergent compositions and washing or cleaning methods without departing from the concepts of the present disclosure, and further it is to be understood that such concepts are intended to be covered by the following claims unless these claims by their language expressly state otherwise.

When forming the detergent compositions of the present disclosure, a container is typically charged with the deionized water first, thereafter, the CARBOMER® is added using a lightning mixer or tri-blender. Once the CARBOMER® is completely hydrated the remaining ingredients are added. Typically, sodium hydroxide is added as the last ingredient. Each ingredient is mixed well between each addition.

Use and Application of Detergent Composition to Wash/Clean Urushiol and Treat Urushiol Induced Contact Dermatitis In use, the detergent compositions of the present disclosure are applied directly or indirectly to the skin or clothing exposed to urushiol after the composition is hydrated, typically by wetting the composition in the user's hands for about 10 seconds until the product is worked into a paste form. The paste is typically a semisolid preparation intended for external application to the skin. Usually, the paste is thick and does not melt at normal/ambient room temperature. The paste formed from the detergent composition should then be rubbed on the affected area of the skin for up to 3 minutes until there is no sign of itching (about 15 seconds is typical for mild to moderate reactions to urushiol). Thereafter, the area should be rinsed thoroughly. If itching returns, the process may be repeated any number of times. Typically, only a few treatments will be necessary. The methods of treating contact dermatitis and the methods of washing skin exposed to urushiol of the present disclosure typically include the above steps.

What is claimed is:

1. A method comprising the steps of:
   applying a non-buffered detergent composition to a surface exposed to urushiol wherein the non-buffered detergent composition comprises a first solely $C_{12}$ surfactant, a second solely $C_{12}$ surfactant, and a non-ionic polyethylene glycol ether of a mixture of synthetic $C_{12}$-$C_{15}$ fatty alcohols with an average of 9 moles of ethylene oxide; and wherein the non-buffered detergent composition is free of each of the following: (1) any nonylphenol ethoxylate, (2) any pharmaceutically active drug or prodrug, (3) any salt that affects the functional characteristics of either of the first solely $C_{12}$ surfactant or the second solely $C_{12}$ surfactant, (4) any salt in granular form, and (5) any ethoxylate added as a separate component and not part of the non-ionic polyethylene glycol ether of a mixture of synthetic $C_{12}$-$C_{15}$ fatty alcohols with an average of 9 moles of ethylene oxide;
   washing an area of the surface by rubbing the non-buffered detergent composition onto the area of the surface exposed to urushiol; and
   rinsing the non-buffered detergent composition from the area of the surface exposed to urushiol.

2. The method of claim 1, wherein the method further comprises the step of forming a paste by adding water to the non-buffered detergent composition to hydrate the non-buffered detergent composition such that the paste is formed.

3. The method of claim 1, wherein the first solely $C_{12}$ surfactant and the second solely $C_{12}$ surfactant are present in a ratio based on a percent of active ingredient in the non-buffered detergent composition in a ratio range of from 1 part first solely $C_{12}$ surfactant to up to 2.5 parts second solely $C_{12}$ surfactant.

4. The method of claim 3, wherein the first solely $C_{12}$ surfactant is sorbitan monolaurate.

5. The method of claim 3, wherein the second solely $C_{12}$ surfactant is sodium lauroyl sarcosinate.

6. The method of claim 2, wherein the washing step lasts between at least 15 seconds to at most 3 minutes.

7. The method of claim 6, wherein the water is a non-ionized water.

8. The method of claim 4, wherein the sorbitan monolaurate is present in the non-buffered detergent composition in an amount of from 2.0 to 10% by weight.

9. The method of claim 5, wherein the sodium lauroyl sarcosinate is present in the non-buffered detergent composition in an amount of from 1.0% to 10.0% by weight of the non-buffered detergent composition.

10. The method of claim 3, wherein a total amount of all solely $C_{12}$ surfactants components in the non-buffered detergent composition is from 1.5% to 60% by weight of the non-buffered detergent composition.

11. The method of claim 1, wherein a pH of the non-buffered detergent composition is from 5.5 to 7.0 and wherein the surface is a surface area of fabric chosen from the group consisting of a skin surface, a towel, blanket, an article of clothing, and a backpack.

12. The method of claim 1, wherein the non-buffered detergent composition does not contain any sodium chloride and wherein the surface is a surface area of fabric chosen from the group consisting of a skin surface, a towel, blanket, an article of clothing, and a backpack.

13. The method of claim 10, wherein non-buffered detergent composition comprises a total amount of solely $C_{12}$ surfactants that is from about 2.9 to about 4.1% by weight of the non-buffered detergent composition.

14. The method of claim 2, wherein the water added to hydrate the non-buffered detergent composition such that the paste is formed is in an amount of 40-60 percent of a weight of the non-buffered detergent composition.

15. A method comprising the steps of:
   applying a non-buffered detergent composition to at least a surface area wherein the surface area is chosen from the group consisting of a skin surface, a towel, blanket, an article of clothing, and a backpack exposed to urushiol wherein the non-buffered detergent composition comprises: non-ionized water; a hydrophilic and cross-linked polyacrylic acid polymer; at least one type of bio-degradable bead having a maximum particle size of 300 microns; a silicone copolyol wetting agent; sorbitan monolaurate; sodium lauroyl sarcosinate; a non-ionic polyethylene glycol ether of a mixture of synthetic $C_{12}$-$C_{15}$ fatty alcohols with an average of 9 moles of ethylene oxide; a preservative; a disodium EDTA; a sodium hydroxide; and wherein the non-buffered detergent composition does not include any of the following: (1) any nonylphenol ethoxylate, (2) any pharmaceutically active drug or prodrug, (3) any granular salt, and/or (4) any salt in an amount that affects the functional characteristics of either sorbitan monolaurate or sodium lauroyl sarcosinate, and (5) any ethoxylate added as a separate component and not part of the non-ionic polyethylene glycol ether of a mixture of synthetic $C_{12}$-$C_{15}$ fatty alcohols with an average of 9 moles of ethylene oxide;

washing the surface area by rubbing the non-buffered detergent composition onto the surface area exposed to urushiol; and rinsing the non-buffered detergent composition from the surface area exposed to urushiol.

16. The method of claim 15, wherein the non-ionic polyethylene glycol ether of a mixture of synthetic $C_{12}$-$C_{15}$ fatty alcohols with an average of 9 moles of ethylene oxide is $C_{12}$-$C_{15}$ Pareth-9.

17. The method of claim 15, wherein the silicone copolyol wetting agent is a dimethylmethyl (polyethylene oxide) siloxane having a hydrophilic-lipophilic balance of 10 or greater.

18. A method of removing urushiol from a surface exposed to urushiol wherein the surface is chosen from the group consisting of a skin surface, a towel, blanket, an article of clothing, and a backpack, the method comprising the steps of:

applying a non-buffered urushiol washing composition to the surface exposed to urushiol wherein the non-buffered urushiol washing composition comprises: non-ionized water; a hydrophilic and cross-linked polyacrylic acid polymer; at least one type of biodegradable bead having a maximum particle size of 300 microns; a silicone copolyol wetting agent; a first solely $C_{12}$ surfactant; a second solely $C_{12}$ surfactant; a non-ionic polyethylene glycol ether of a mixture of synthetic $C_{12}$-$C_{15}$ fatty alcohols with an average of 9 moles of ethylene oxide; a preservative; a disodium EDTA; wherein the non-buffered urushiol washing composition does not include any of the following: (1) any nonylphenol ethoxylate, (2) any pharmaceutically active drug or prodrug, (3) any granular salt, and/or (4) any salt in an amount that affects the functional characteristics of either sorbitan monolaurate or sodium lauroyl sarcosinate and (5) any ethoxylate added as a separate component and not part of the non-ionic polyethylene glycol ether of a mixture of synthetic $C_{12}$-$C_{15}$ fatty alcohols with an average of 9 moles of ethylene oxide; wherein the first solely $C_{12}$ surfactant and the second solely $C_{12}$ surfactant are present in a ratio based on a percent of active ingredient in the non-buffered urushiol washing composition in a ratio range of from 1 part first solely $C_{12}$ surfactant to up to 2.5 parts second solely $C_{12}$ surfactant;

washing the surface exposed to urushiol by rubbing the non-buffered urushiol washing composition onto the surface exposed to urushiol; and rinsing the non-buffered urushiol washing composition from the surface exposed to urushiol.

19. The method of claim 18, wherein the silicone copolyol wetting agent is PEG-12 dimethicone and is present in an amount of 0.8% to 1.2% by weight of the non-buffered urushiol washing composition.

20. The method of claim 18, further comprising sodium hydroxide in an amount to neutralize the hydrophilic and cross-linked polyacrylic acid polymer.

* * * * *